US009110077B2

(12) United States Patent
Martineau et al.

(10) Patent No.: US 9,110,077 B2
(45) Date of Patent: Aug. 18, 2015

(54) METHOD FOR IDENTIFYING A LIGAND CAPABLE OF SELECTIVELY MODULATING A FUNCTIONAL CASCADE INVOLVING A TARGET, AND USES THEREOF FOR HIGH-THROUGHPUT SCREENING OF MOLECULES OF INTEREST

(75) Inventors: Pierre Martineau, Saint Gely du Fesc (FR); Piona Dariavach, Montpellier (FR)

(73) Assignees: Centre National de la Recherche Scientifique, Paris (FR); Universite de Montpellier, Montpellier (FR)

( * ) Notice: Subject to any disclaimer, the term of this patent is extended or adjusted under 35 U.S.C. 154(b) by 1913 days.

(21) Appl. No.: 11/568,375

(22) PCT Filed: Apr. 25, 2005

(86) PCT No.: PCT/FR2005/001020
§ 371 (c)(1),
(2), (4) Date: Aug. 20, 2007

(87) PCT Pub. No.: WO2005/106481
PCT Pub. Date: Nov. 10, 2005

(65) Prior Publication Data
US 2008/0146453 A1      Jun. 19, 2008

(30) Foreign Application Priority Data
Apr. 27, 2004   (FR) ..................................... 04 04433

(51) Int. Cl.
*C12Q 1/02*      (2006.01)
*C40B 30/04*    (2006.01)
(Continued)

(52) U.S. Cl.
CPC ............ *G01N 33/6854* (2013.01); *C12Q 1/025* (2013.01); *G01N 33/5041* (2013.01);
(Continued)

(58) Field of Classification Search
CPC ................................ C12Q 1/025; C12Q 1/485
See application file for complete search history.

(56) References Cited

U.S. PATENT DOCUMENTS 5,858,657 A  *  1/1999  Winter et al. ...................... 435/6
6,143,876 A  *  11/2000 Gershoni ................. 530/388.35
(Continued)

FOREIGN PATENT DOCUMENTS

WO     WO 00/54057       *  9/2000  ............. G01N 33/68
WO     WO 01/01137 A        1/2001
(Continued)

OTHER PUBLICATIONS

Green (BioTechniques, 2001, 30:1094-1110).*
(Continued)

*Primary Examiner* — Christopher M Babic
*Assistant Examiner* — Jeremy C Flinders
(74) *Attorney, Agent, or Firm* — Alston & Bird LLP

(57) ABSTRACT

The invention concerns a method for identifying a ligand capable of selectively modulating a functional cascade involving a target, and uses thereof for high-throughput screening of molecules of interest, in particular therapeutic (medicine). Said method comprises at least the following steps: a) identifying an antibody or an antibody fragment comprising at least one of the variable domains of an immunoglobulin chain, capable of binding to said target and modulating said functional cascade involving said target; b) screening from a bank of molecules, ligands modulating the bond between said target and the antibody or antibody fragment identified in a); and c) identifying among said modulating ligands obtained in b), those capable of modulating said functional cascade.

11 Claims, 5 Drawing Sheets

(51) Int. Cl.
*G01N 33/68* (2006.01)
*G01N 33/50* (2006.01)
*C40B 40/02* (2006.01)
*C07K 16/00* (2006.01)

(52) U.S. Cl.
CPC .......... *G01N33/686* (2013.01); *G01N 33/6872* (2013.01); *C07K 2317/622* (2013.01); *G01N 2500/00* (2013.01)

(56) References Cited

U.S. PATENT DOCUMENTS

| | | | |
|---|---|---|---|
| 7,122,630 B1 * | 10/2006 | Luo et al. | 530/350 |
| 7,244,592 B2 * | 7/2007 | Hoogenboom et al. | 435/69.7 |
| 7,569,390 B1 * | 8/2009 | Eric et al. | 506/9 |
| 2003/0224408 A1 * | 12/2003 | Hoogenboom et al. | 435/6 |

FOREIGN PATENT DOCUMENTS

| | | | | |
|---|---|---|---|---|
| WO | WO 01/21654 | * | 3/2001 | C07K 14/00 |
| WO | WO 03/059943 | * | 7/2003 | C07K 11/00 |
| WO | WO 03/059943 A | | 7/2003 | |
| WO | WO 2004/020619 A | | 3/2004 | |
| WO | WO 2004/046192 A | | 6/2004 | |

OTHER PUBLICATIONS

Kay (Comb. Chem. & High Throughput Screening, 2001, 4:535-543).*
Lapan (Expert Opin. Ther. Targets, 2002, 6:507-516).*
Hyde-DeRuyscher (Chem. Biol., 2000, 7:17-25).*
Soni (Journal of the National Cancer Institute, 2001, 93:436-446).*
Dauvillier S. et al., "Intracellular single-chain variable fragments directed to the Src homology 2 domains of Syk partially inhibit FcepsilonRl signaling in the RBL-2H3 cell line", Journal of Immunology, The Williams and Wilkins Co., vol. 169, No. 5, Sep. 1, 2002, pp. 2274-2283.
Krebs B. et al., "High-throughput generation and engineering of recombinant human antibodies", Journal of Immunological Methods, Elsevier Science Publishers, vol. 254, No. 1-2, Aug. 1, 2001, pp. 67-84.

* cited by examiner

METHOD FOR IDENTIFYING A LIGAND CAPABLE OF SELECTIVELY MODULATING A FUNCTIONAL CASCADE INVOLVING A TARGET, AND USES THEREOF FOR HIGH-THROUGHPUT SCREENING OF MOLECULES OF INTEREST

FIELD AND BACKGROUND OF THE INVENTION

The present invention relates to a method for identifying a ligand capable of selectively modulating a functional cascade involving a target molecule or target, and also to uses thereof for high-throughput screening of molecules of interest, in particular therapeutic interest (medicament).

Recent advances in the fields of genomics and proteomics, which have led to the identification of a considerable number of new potential therapeutic targets, have opened up very interesting perspectives in the pharmaceutical field.

However, the discovery of new medicaments involves developing methods for high-throughput screening of libraries of molecules which are effective, i.e. which make it possible to isolate, from a restricted number of selected molecules (hits), molecules which are active in vivo on the pathology intended to be treated (leads).

In fact, functional tests (in vitro in cell culture or in vivo in an appropriate animal model) which make it possible to verify the activity of the hits selected during the screening are not generally adaptable to high-throughput.

Since most eukaryotic proteins are multifunctional and involved in several functional cascades, the molecules isolated must be capable of specifically modulating the property of interest of the target without affecting its other activities, the modulation of which could have detrimental effects for the cell. Consequently, the screening must be highly specific in order to restrict to a maximum the number of hits identified, so that only a small number of them have to be tested in functional tests in vivo.

These screening methods must also be easy to carry out and be applicable to any target.

With this aim, screening methods based on the identification of molecules (mimotopes) that mimic the interaction between the target and a peptide or an oligonucleotide (aptamer) have been proposed.

Screening methods using aptamers and/or peptides are illustrated in Lapan et al., Expert Opin. Ther. Targets, 2002, 6, 507-516; Green et al., BioTechniques, 2001, 30, 1094-1110; Burgstaller et al., Drug Discovery Today, 2002, 7, 1221-1228; PCT international applications WO 98/19162 and WO 03/059943 and American U.S. Pat. No. 6,329,145.

In a first step, aptamers/peptides capable of binding to the target are selected in vitro, and then their modulatory activity with respect to the target is verified by means of a functional test in vitro in an appropriate cell system or in vivo in an appropriate animal model.

In a second step, the aptamers/peptides that have a modulatory activity on the target are used in competitive binding assays for identifying hits capable of displacing the existing binding between the aptamer/peptide and the target. The modulatory activity of the hits with respect to the target is subsequently verified by means of a functional test in vitro in cell culture or in vivo in an appropriate animal model, so as to isolate "lead" molecules.

These methods have been validated with targets such as the BB isoform of human platelet-derived growth factor (PDGF BB) and the human immunodeficiency virus (HIV) Rev protein.

The inventors have given themselves the aim of developing alternative screening methods. They have shown that substitution of the modulatory aptamers or peptides with modulatory antibodies or antibody fragments, in the screening methods as described in the prior art, makes it possible to identify molecules capable of selectively modulating a functional cascade involving a target (metabolic cascade, activation cascade, signaling cascade, etc.).

Antibodies have the advantage of recognizing any region of a protein, specifically and with a high affinity (of the order of 1 nM). In particular, they can recognize the surface sites of this protein and are therefore very advantageous for specifically inhibiting the regions of proteins involved in functional cascades via protein-protein interactions; it has in particular been shown that antibody fragments (scFv) directed against the SH2 domains of the Syk protein tyrosine kinase are capable of specifically inhibiting, in vivo, the phospholipase C-γ2 pathway (PLC-γ2; Dauvilliers et al., J. Immunol., 2002, 169, 2274-2283). Consequently, the mimotopes isolated by means of a screening method using antibodies or antibody fragments should have the same properties, in particular in terms of affinity/specificity for the target.

For example, the inventors have screened a library of 3000 molecules using an antibody directed against the SH2 domains of the Syk protein tyrosine kinase and capable of inhibiting the PLCγ-2 pathway; among the 10 ligands of the Syk protein that they selected, at least one was an inhibitory molecule in vivo, acting on the PLC-γ2 pathway, without impairing the Ras pathway, which is also dependent on the Syk protein.

Conversely, it has not been demonstrated that aptamers and peptides are capable of recognizing any surface epitope of an antigen. By virtue of their small size, peptides and aptamers are more suitable for interacting in the cavities of targets rather than at the surface, which is favorable for inhibiting an enzymatic activity but not very advantageous for inhibiting functional cascades.

Moreover, a certain number of recombinant monoclonal antibodies are used in therapeutic treatments. Mention may, for example, be made of cetuximab (anti-EGFR), rituximab (anti-CD20), infliximab (anti-TNF), etc. These antibodies are either chimeric antibodies, most commonly mouse/human, or humanized antibodies. These antibodies are difficult to produce and are very expensive. The screening method proposed by the inventors makes it possible to substitute these antibodies with chemical molecules having the same inhibitory properties, that are easier to produce and at a much lower cost (by at least a factor of 10).

SUMMARY OF THE INVENTION

Consequently, a subject of the present invention is a method for identifying a ligand capable of selectively modulating a functional cascade involving a target, characterized in that it comprises at least the following steps:

a) identifying an antibody or an antibody fragment comprising at least one of the variable domains of an immunoglobulin chain, capable of binding to said target and of modulating said functional cascade involving said target, b) screening, using a library of molecules, ligands that modulate the binding between said target and the antibody or the antibody fragment identified in a), and c) identifying, from the modulatory ligands obtained in b), those capable of modulating said functional cascade.

The steps of the method according to the invention as defined above are described schematically in FIG. 1.

DEFINITIONS

The term:

"functional cascade" is intended to mean a metabolic pathway, a signaling pathway or an activation cascade involving a succession of reactions (enzymatic reactions, molecular interactions, conformational changes, chemical modifications) in a cell, each of the reactions being dependent on the preceding ones and resulting in a measurable biological activity in said cell, "modulation" is intended to mean a positive or negative modulation: total or partial activation or inhibition, "target involved in a functional cascade" is intended to mean any molecule of a cell of an organism (human, animal, plant) or of a microorganism (virus, bacterium, fungus, parasite) which is capable of interacting with one or more ligands (or known or unknown natural partners), each binding to a distinct site or region of said target (FIG. 2); the binding of the ligand modulates a functional cascade involved in a physiological or pathological process of said cell or of said microorganism and results in a measurable biological activity in said cell or said microorganism. Said target may in particular be: a protein, a peptide, a polynucleotide (DNA, RNA), a lipid, a sugar or a derivative of the above (glycoprotein, glycolipid, etc.).

FIG. 3 illustrates the example of the Syk protein tyrosine kinase (PTK), which is a multifunctional protein involved, inter alia, in two activation cascades: the first (cascade 1), which results in activation of the Ras protein and then of MAPK, is involved in the growth and differentiation of certain cells of the lymphoid line, including B lymphocytes, mast cells, basophiles and a subpopulation of T lymphocytes (first biological activity), and the second (cascade 2), which results in the activation of the PTK Btk and of phospholipase C-γ2 (PLCγ-2) and in increased intracellular calcium flux, results in degranulation and the release of allergic mediators by mast cells (second biological activity). The functional cascade intended to be selectively inhibited is cascade 2, which has uses in the prevention and/or treatment of allergies, whereas cascade 1 must not be inhibited since it could result in side effects harmful to the cells (tumor aggressiveness; Coopman et al., Nature, 2000, 406, 742-747), "library of molecules" or combinatorial library is intended to mean a set of molecules other than antibodies or antibody fragments, related by virtue of their structure, their origin or their function, in particular a combinatorial library including molecules which differ from one another by virtue of the systematic or random replacement of their elementary constituents, for example a library of oligomers such as peptides, oligonucleotides (aptamers) and oligosaccharides, or else a library of cyclic or noncyclic organic molecules, other than oligomers, in particular small organic molecules, i.e. having a molecular mass of less than 2500 Da, preferably less than 2000 Da, preferably less than 1500 Da, more preferably less than 1000 Da, even more preferably less than 750 Da, "antibody fragment" is intended to mean a fragment capable of binding to a target, comprising at least the variable domain of a heavy chain (VH) and/or the variable domain of a light chain (VL) of a conventional immunoglobulin, or else the variable domain of a single-chain immunoglobulin, such as Fab, Fv, scFv or VHH fragments, "antibody or antibody fragment capable of binding to said target and of modulating the functional cascade involving said target" is intended to mean an antibody or an antibody fragment capable of binding to said target and of mimicking the interaction in vivo of said target with its ligand (natural partner), at the site of interest; the epitope of the target recognized by said antibody or antibody fragment partially or totally overlaps the site of interest of said target (FIG. 2B).

The screening of the library of molecules [step b)] or of a library of antibodies or antibody fragments [step a) for identifying antibodies or antibody fragments capable of binding to the target] are carried out by any method known to those skilled in the art for measuring the interaction between two partners (ELISA, resonance energy transfer (FRET), fluorescence polarization, surface plasmon resonance). Steps a) and b) are carried out using a target or a derivative of the target, such as a fragment comprising at least the site of interest, a mimotope, or alternatively an anti-idiotype antibody representing the internal image of said site of interest of the target. Said target and derivatives its or else the antibody or the antibody fragment are optionally immobilized on an appropriate support and/or labeled by any means for obtaining a measurable signal, known to those skilled in the art.

The identification of the ligands or else of the antibodies or antibody fragments capable of selectively modulating a functional cascade involving said target is carried out by means of a functional test for measuring the biological activity resulting from said functional cascade. It is, in particular, an in vitro test, in an appropriate cell system, or an in vivo test, in an appropriate organism.

The cells in culture can be immortalized, or can be in a primary culture, and can be adherent or in suspension. The living organism can be any laboratory or study organism or microorganism (animal (rodents, rabbits, pigs, cattle, members of the ovine family, etc.) or transgenic or nontransgenic plant, parasite, etc.).

Among the appropriate cell systems and organisms, mention may in particular be made of those which are models of the physiological or pathological process involving said functional cascade, such as, in a nonlimiting manner, models of diabetes, of allergy, of arthritis or of asthma.

Advantageously, the identification of the antibodies or antibody fragments capable of modulating a functional cascade involving said target is carried out in cells modified with a vector for expression of said antibodies or of their fragments (antibodies or antibody fragments that are intracellular).

The functional test used in this verification in vitro, in a cell system, or in vivo, in an appropriate organism, depends on the biological activity that it is being sought to modulate for a therapeutic or nontherapeutic purpose. By way of nonlimiting example of a measurable biological activity in cells, mention may in particular be made of: division, migration, degranulation, transport through membranes, differentiation, apoptosis, replication, transcription and production of factors such as cytokines. The functional tests for measuring said biological activity in vitro or in vivo are known to those skilled in the art.

According to an advantageous embodiment of said method, the identification of said antibody or antibody fragment in a) is carried out by screening a library of antibodies or antibody fragments, preferably a library of scFv fragments, preferably a library of phages expressing scFv fragments at their surface.

The identification of said antibody can comprise:
a first step consisting in screening antibodies or antibody fragments capable of binding to said target, in particular by phage-ELISA, and
a second step consisting in identifying the antibodies or antibody fragments capable of modulating said functional cascade, in particular in cells modified with a vector for expression of said antibodies or antibody fragments (antibodies or antibody fragments that are intracellular).

More specifically, the antibodies or the antibody fragments, in particular the scFv fragments, selected during the screening step can then be cloned into an appropriate vector and expressed in cells, in particular eukaryotic cells such as mammalian cells modified with the recombinant vector thus obtained. Such antibodies or antibody fragments, called intracellular antibodies (Cattaneo et al., Trends in Biotechnology, 1999, 17, 115-121), are expressed in functional form, capable of binding to the target in the compartment of the modified cells in which it is expressed (nucleus, cytoplasm, secretory compartment). In addition, mutations can be introduced into the sequence of the antibodies or of the antibody fragments selected, so as to improve their solubility and/or their conformation in the cells, in particular in eukaryotes. Among the mutations that can be envisioned, mention may in particular be made of the point mutations described in Hurle et al., PNAS USA, 1994, 91, 5446-5450 and Martineau et al., J. Mol. Biol., 1998, 280, 117-127. In addition, antibodies or antibody fragments exhibiting increased stability and/or affinity can be selected by means of an additional phenotypic selection step, as described in Cattaneo et al., mentioned above.

Alternatively, the identification of the antibodies or antibody fragments capable of modulating said functional cascade is carried out by means of an appropriate phenotypic selection of cells modified with a library of antibodies or of antibody fragments, according to the principle as described in Cattaneo et al., mentioned above.

According to another advantageous embodiment of said method, the screening step b) comprises:
bringing the library of molecules to be tested into contact with the target or one of its derivatives as defined above,
adding the antibody or the antibody fragment, optionally labeled, and
measuring, by any appropriate means, the relative amount of antibody bound to the target, in the presence or absence of said library of molecules.

According to another advantageous embodiment of said method, the screening step b) is carried out by means of a test for binding of said target, in competition with said antibody or said antibody fragment, so as to isolate ligands of said target which displace said antibody or said antibody fragment from the target/antibody or antibody fragment complex.

An example of this embodiment comprises:
bringing the optionally labeled antibody or antibody fragment into contact with the target or one of its derivatives as defined above,
adding the library of molecules to be tested so as to detect the molecules capable of displacing the antibody or antibody fragment from its complex with the fragment of the target, and
measuring, by any appropriate means, the relative amount of antibody bound to the target, in the presence or absence of said library of molecules.

Another example of this embodiment comprises:
mixing the optionally labeled antibody or antibody fragment with the library of molecules to be tested,
bringing the mixture into contact with the target or one of its derivatives as defined above, and
measuring, by any appropriate means, the relative amount of antibody bound to the target, in the presence or absence of said library of molecules.

The ability of a molecule to modulate the binding between the target and the antibody is determined by comparing the value of the antibody binding signal, in the presence or absence of each of the molecules of the library, tested separately.

According to another advantageous embodiment of said method, steps a) and c) are carried out by means of a functional test for measuring the biological activity resulting from said functional cascade, in particular by means of an in vitro test, in an appropriate cell system, or an in vivo test, in an appropriate organism.

According to another advantageous embodiment of said method, said target is selected from: an enzyme, a receptor, an adaptor protein, a transporter, a chaperone protein and a regulatory protein.

By way of nonlimiting example of these proteins, mention may be made of: enzymes such as protein tyrosine kinases, for instance the Syk protein; cytokine receptors such as the IL-13 receptor, the EGF receptor or the TNF receptor, adaptor proteins such as SLP-76 and E6-AP; chaperone proteins such as HSP70 and HSP60; and regulatory proteins such as NF-κB, I-κB, Akt, PSAT-1, p53, p73 and the Bcl2 family.

According to yet another advantageous embodiment of said method, said antibody or antibody fragment in a) is directed against the SH2 domains of the Syk protein and is capable of inhibiting the PLCγ-2 pathway. Such an antibody makes it possible to identify medicaments that act specifically on type 1 hypersensitivity reactions, which can be used for the prevention and/or treatment of pathologies such as conjunctivitis or allergic rhinitis, extrinsic asthma, Quincke's edema and anaphylactic shock, in the most serious of cases.

According to another advantageous embodiment of said method, said library of molecules in b) is a library of small organic molecules.

A subject of the present invention is also a kit for carrying out the method as defined above, characterized in that it comprises at least:
a target involved in a functional cascade, a fragment of said target comprising at least the site of interest, a mimotope of said target, or else an anti-idiotype antibody representing the internal image of said site of interest of the target, as defined above,
an antibody or an antibody fragment comprising at least one of the variable domains of an immunoglobulin chain, capable of binding to said target and of modulating said functional cascade involving said target or a library of antibodies or of antibody fragments, as defined above, and
a library of molecules to be tested, as defined above.

The method according to the invention can be used to screen any type of molecule of therapeutic or nontherapeutic interest, capable of acting on a physiological or pathological process of any type of cell or of microorganism, as defined above.

It can be used to screen novel families of molecules exhibiting novel properties of therapeutic or nontherapeutic interest or derivatives of these molecules exhibiting an improved specific activity and/or an improved therapeutic index.

The libraries of molecules are prepared according to the conventional methods of combinatorial chemical synthesis, known to those skilled in the art.

The antibody or the antibody fragment as defined above is prepared by conventional techniques known to those skilled in the art, such as those described in *Antibodies: A Laboratory Manual*, E. Howell and D Lane, Cold Spring Harbor Laboratory, 1988. More specifically:

the monoclonal antibodies are produced from hybridomas obtained by fusion between B lymphocytes from an immunized animal and myelomas, according to the technique of Köhler and Milstein (Nature, 1975, 256, 495-497); the hybridomas are cultured in vitro, in particular in fermenters, or produced in vivo, in the form of ascites; alternatively, said monoclonal antibodies are produced by genetic engineering, as described in *Methods in Molecular Biology: Antibody Phage Display Methods and Protocols*, P. M. O'Brien and R. Aitken. Humana Press, Vol. 178, 2002. For example, suitable animals are immunized repeatedly with the target or one of its fragments, according to a standard protocol comprising a first immunization by intraperitoneal injection of the antigen in an equivalent volume of complete Freund's adjuvant, and then a second immunization (booster) 15 days later, under identical conditions but this time with incomplete Freund's adjuvant. The monoclonal antibodies are produced according to a standard protocol comprising sacrifice of the animals two weeks after the final booster, removal of the spleen, suspension of the spleen lymphocytes and fusion of these lymphocytes with the SP2/0 murine cell line, which does not produce any murine antibodies, which is immortalized, and which has all the machinery required for the secretion of immunoglobulins;

the libraries of antibodies are either natural libraries produced from the $V_H$ and $V_L$ regions cloned from the mRNAs of hybridomas or of spleen lymphocytes from naïve or preimmunized individuals, or recombinant libraries; for example, the Fv, scFv or Fab fragments are expressed at the surface of filamentous phages according to the technique initially described in Winter and Milstein, Nature, 1991, 349, 293-299 (*Methods in Molecular Biology: Antibody Phage Display Methods and Protocols*, P. M. O'Brien and R. Aitken. Humana Press, Vol. 178, 2002; Knappik et al., J. Mol. Biol., 2000, 296, 57-86; Vaughan et al., Nature Biotech, 1996, 14, 309-314);

the target-specific antibodies are isolated by screening the libraries as defined above, in particular the phage libraries; after several selection steps, the phages which express the target-specific antibody fragments are isolated and the cDNAs corresponding to said fragments are expressed in an appropriate expression system, by means of the conventional techniques for cloning and expression of recombinant DNA. Preferably, said cDNAs are cloned into both a prokaryotic expression vector and a eukaryotic expression vector, in the form of a fusion protein comprising, at least at its —NH$_2$ or COOH end, a tag for the detection of said antibody fragment, for example an epitope (c-myc, HA). Said fusion protein can optionally comprise, at one of the ends, a tag for the purification of the antibody fragment, for example a polyhistidine sequence for purification on a nickel-agarose column. Said eukaryotic expression vector contains, in addition to the appropriate regulatory elements for transcription/translation (promoter, enhancer, Kazaks consensus sequence, polyadenylation signal, etc.) under the control of which are inserted the coding sequences as defined above, the elements essential for the expression of said fragments in the appropriate cell compartment as defined above, in particular in the cytoplasm, and, optionally, a selectable marker (gene for resistance to an antibiotic, etc.) for the selection of cell lines, in particular eukaryotic cell lines, stably modified with said expression vector and producing the intracellular antibodies.

The monoclonal antibodies or their fragments as defined above are purified by conventional techniques known to those skilled in the art, in particular by affinity chromatography.

The target or the fragment comprising the site of interest can be either purified from tissues or from cells, by conventional techniques known to those skilled in the art, or produced by conventional recombinant DNA techniques known to those skilled in the art, according to standard protocols such as those described in particular in *Current Protocols in Molecular Biology* (Frederick M. AUSUBEL, 2000, Wiley and son Inc, Library of Congress, USA). The polynucleotide encoding said protein or said fragment is cloned into an expression vector (plasmid, virus, etc.) in which said polynucleotide is placed under the control of appropriate regulatory elements for transcription of the translation. In addition, said vector can comprise (tag) sequences fused in-frame with the 5' and/or 3' end of said polynucleotide, that can be used for the immobilization and/or the detection and/or the purification of the protein expressed from said vector; said protein is then expressed in appropriate host cells (bacteria, yeasts, insect cells or mammalian cells) and, optionally, purified.

Alternatively, the fragment comprising the site of interest is synthesized in solid phase, according to the method initially described by Merrifield et al. (*J. Am. Chem. Soc.*, 1964, 85: 2149-).

The labeling of the target, of the antibody or of its fragment and the detection of the antibody/target and ligand/target binding are carried out by conventional techniques known to those skilled in the art: (i) by fusion of the coding sequence with the sequence of an epitope (c-myc, HA), (ii) by coupling with an appropriate label such as a fluorophore, an enzyme (alkaline phosphatase, peroxidase), a radioactive isotope or biotin, (iii) by means of a labeled secondary antibody or else by means of any specific interaction with an appropriate label. For example, the antibody/target and ligand/target binding is detected by fluorescence transfer between two complementary fluorescent proteins (Philipps et al., J. Mol. Biol., 2003, 327, 239), two complementary fluorophores (fluorescein/tetramethylrhodamine) or a combination of the two. For example, said target or said fragment comprises an acceptor or donor fluorophore respectively at its NH$_2$ and/or COOH end, and the antibody or the antibody fragment comprises the complementary fluorophore at its NH$_2$ and/or COOH end.

The method according to the invention has the following advantages:

It makes it possible to identify novel molecules that act selectively and specifically on a physiopathological process, and that can be potentially used as a medicament, via the combination of two screening steps:

a step consisting in screening, by means of a binding assay, that can be readily automated and is suitable for high-throughput, molecules which mimic the interaction of a target with an antibody or an antibody fragment (idiotypic approach) and are therefore capable of modulating the functional cascade involving said target, and a step consisting of low-throughput screening, by means of a functional test in cell culture or in an appropriate animal model, of molecules capable of modulating the functional cascade involving said target, in particular by measuring the biological activity resulting from said cascade.

For example, in the case of the Syk protein tyrosine kinase, the results obtained from a library of 3000 molecules show that the efficiency of the first screening step with the anti-Syk antibody is such that the second functional screening step on a restricted number of molecules (10 molecules) makes it possible to isolate at least one inhibitory molecule that is active in vivo on the functional cascade selected;

insofar as it uses an idiotypic approach, it has the following advantages, namely:
  it is suitable for all cell targets,
  it is suitable for the specific and high-affinity (of the order of 1 nM) recognition of any site of a target of interest, and in particular a site at the surface of said target, capable of binding a partner by means of an interaction of the protein-protein type; consequently, the ligands isolated by means of this screening method should have the same properties, in particular in terms of affinity/specificity for the target,
  it does not entail knowledge of the natural partner of which the interaction with the target is mimicked by the antibody and the ligand selected from the library of molecules, and
  it makes it possible to identify novel molecules for advantageously replacing the recombinant monoclonal antibodies used in therapeutic treatments, such as cetuximab (anti-EGFR), rituximab (anti-CD20) and infliximab (anti-TNF), which are difficult to produce and are expensive.

BRIEF DESCRIPTION OF THE DRAWINGS

Besides the above arrangements, the invention also comprises other arrangements which will emerge from the following description, which refers to examples of screening molecules capable of selectively modulating mast cell degranulation using an scFv fragment directed against the SH2 domains of the Syk target, of the PTK (protein tyrosine kinase) family, and also to the attached drawings in which.

EXAMPLE

Example: Use of an scFv Fragment Directed Against the SH2 Domains of the Syk Protein for Screening Molecules Capable of Inhibiting the PLC-γ2 and Btk Tyrosine Kinase Activation Cascade, which Results in Mast Cell Degranulation and in the Release of Inflammation Mediators The Syk protein is a multifunctional protein tyrosine kinase which plays an important role in the activation of certain cells of the lymphoid line, including B lymphocytes, mast cells and basophils, and a subpopulation of T lymphocytes. Activation of the mast cell line, following recognition by the IgE receptor (FcεRI) of IgEs associated with an allergen, results in the release of allergic mediators such as histamine and serotonin.

Figure 1:
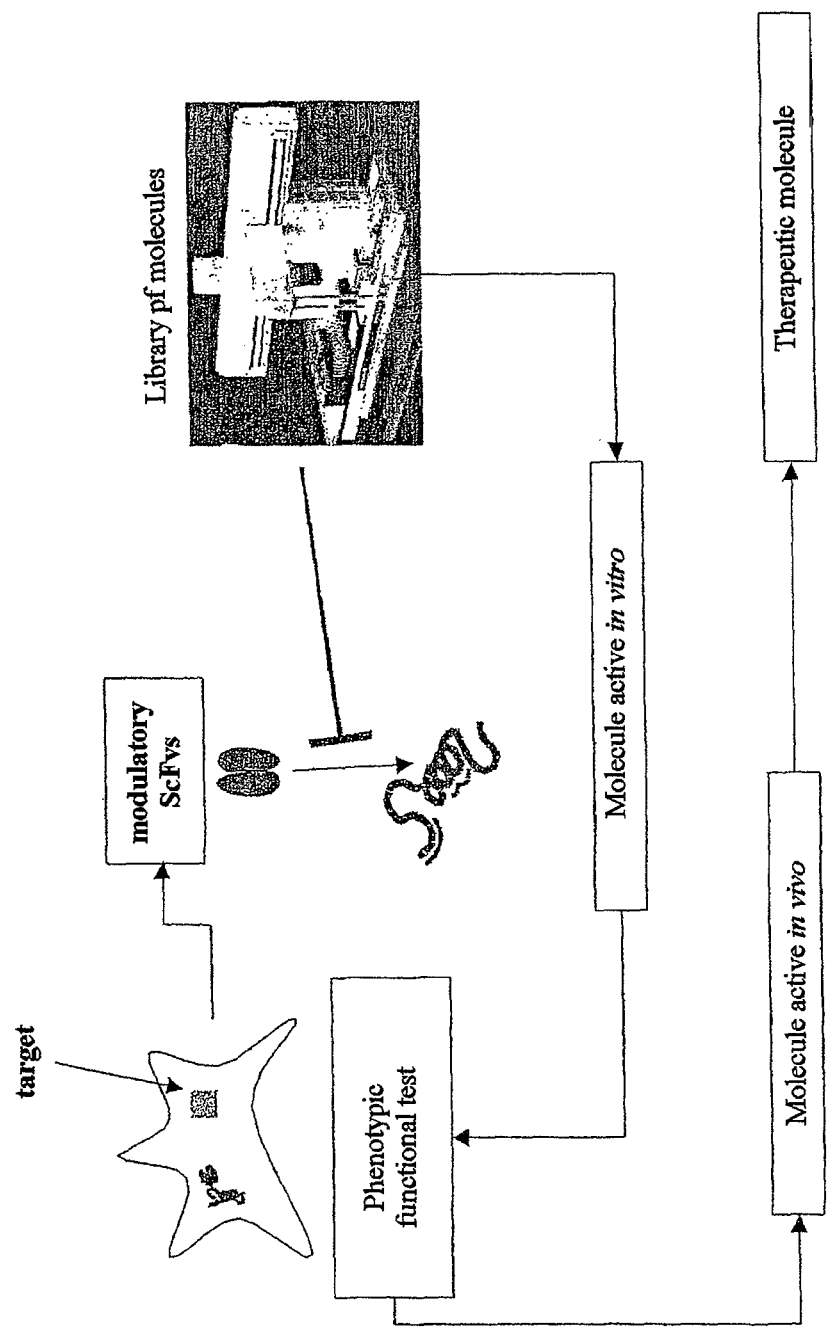
FIG. 1 is a schematic representation of the method according to the invention.
Figure 2:
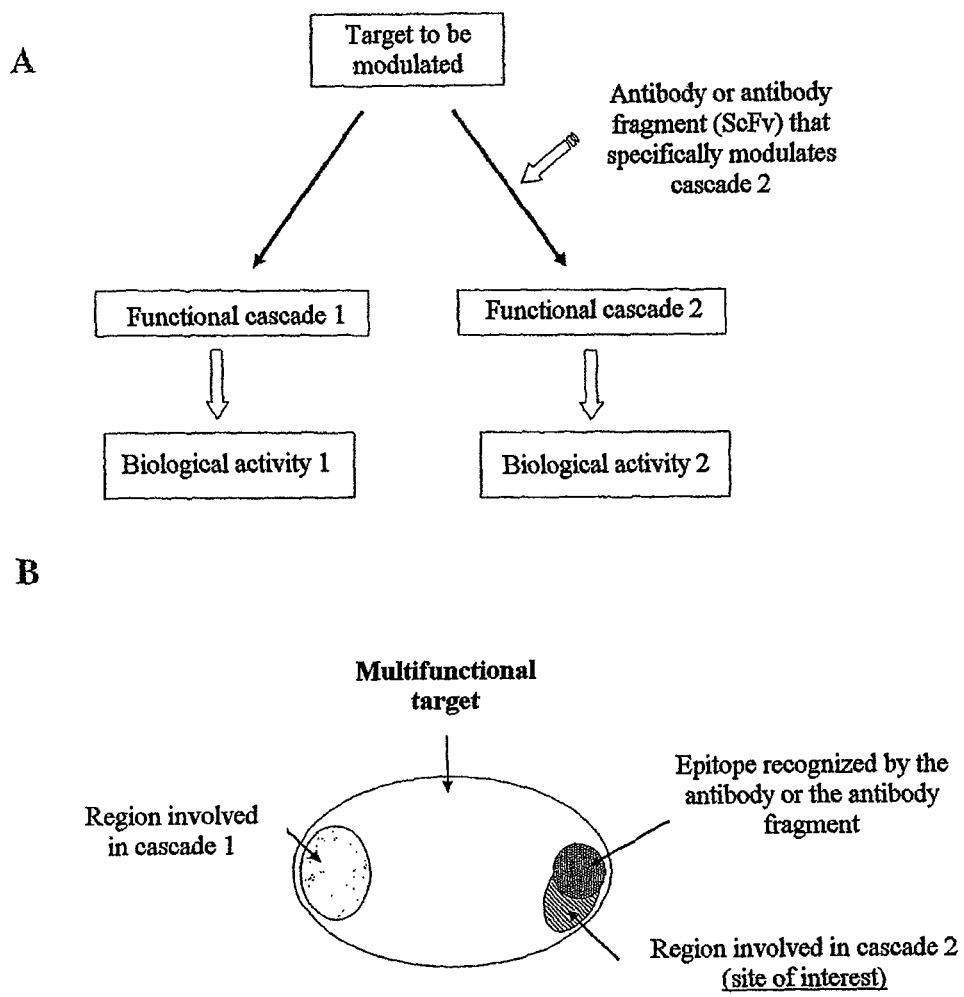
FIG. 2 is a schematic representation of a target and of the functional cascade in which it is involved.
Figure 3:
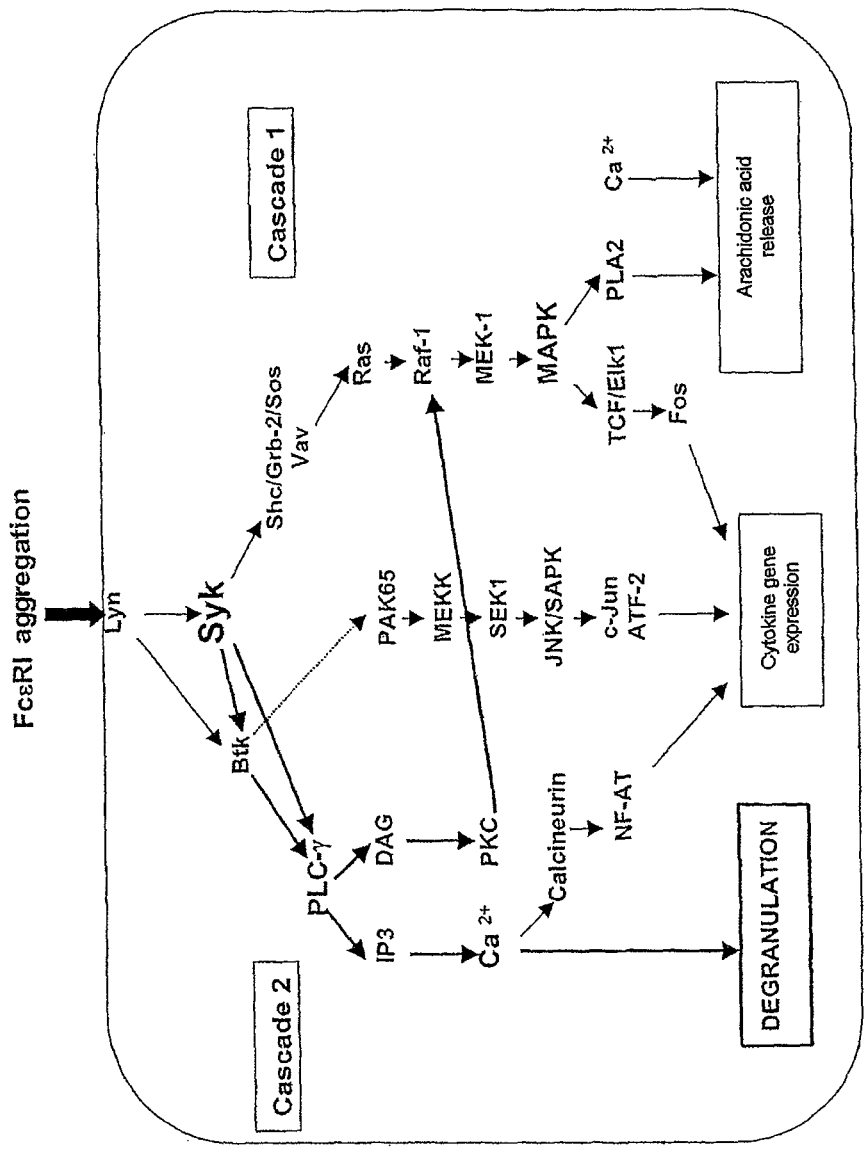
FIG. 3 is a schematic representation of the activation cascades involving the Syk protein tyrosine kinase and of the resulting biological activities.

More specifically, aggregation of the FcεRI receptor rapidly brings about the phosphorylation of the Syk protein and activation thereof. Syk thus activated in turn phosphorylates its cytoplasmic substrates, including the Btk protein tyrosine kinase and phospholipase C-γ2 (PLC-γ2) both involved in the activation cascade which results in mast cell degranulation and the release of allergic mediators (PLC-γ2 pathway; FIG. 3).

The Syk protein is involved in a second pathway (FIG. 3), which results in activation of the Ras protein and then MAP kinase (MAPK). It is important not to disturb this pathway since it has been shown that it is involved in cell growth and differentiation and that modification of this second pathway could lead to malignant phenomena.

Prior studies have made it possible to show that two scFvs that interact with the SH2 domains are capable of specifically inhibiting, in vivo, the PLC γ-2 pathway (G4G11, G4E4; Dauvillier et al., J. Immunol., 2002, 169, 2274-2283). The G4G11 antibody has been used to screen small organic molecules capable of specifically inhibiting this pathway, in vivo.

1) Screening a Library of Molecules by ELISA
a) Materials

The recombinant Syk protein containing two SH2 domains fused with the C-terminal end of glutathione-S-transferase (GST) is produced in *E. coli* and purified as described in Peneff et al., mentioned above.

The anti-Syk human scFv antibody fragment called G4G11, containing, at the C-terminal end, a c-myc tag for detection using an antibody and a polyhistidine tag for purification by affinity chromatography, is produced in *E. coli* and purified as described in Peneff et al., mentioned above.

The secondary antibody is the monoclonal antibody 9E10 directed against the c-myc epitope (EQKLISEEDLN), coupled to peroxidase (Munro et al., Cell, 1986, 46, 291-300).

The library of molecules to be tested is a library of 3000 small organic molecules (ChemBridge Corporation.

All the dilutions and incubations were carried out in a PBS/0.1% Tween 20/0.1% BSA buffer.

The washes were carried out in a PBS/0.1% Tween 20 buffer.

The substrate is tetramethylbenzidine dihydrochloride at 0.1 mg/ml in a phosphate citrate buffer, pH 5, to which $H_2O_2$ (0.03%) has been added.

b) Protocol

The recombinant Syk protein (10 µg/ml in PBS) was adsorbed onto a 96-well plate (Maxisorp®, NUNC; 100 µl, i.e. 1 µg per well), overnight at 4° C. After a first wash, the nonspecific sites on the plate were saturated with a solution of PBS/1% BSA at a rate of 250 μl per well, overnight at ambient temperature. After washing the excess saturation solution, the molecules of the library (3000 molecules) were added at the concentration of 20 μM in a volume of 50 μl and the plates were incubated for 1 hour at ambient temperature. The scFv fragment was then added at the concentration of 150 nM in a volume of 50 μl and the plates were incubated for 1 hour at ambient temperature. After a further wash, 50 μl of peroxidase-labeled secondary antibody were added and the wells were incubated for 30 minutes at ambient temperature. After a final wash, the peroxidase reaction substrate was added in a volume of 100 μl, and the plates were then incubated for 5 minutes and the reaction was stopped by adding 50 μl of 2N $H_2SO_4$. The optical density at 450 nM was then measured using an automatic ELISA plate reader.

The library was screened twice in independent experiments.

c) Results

The inhibition of the binding between the fragment of the Syk protein and the G4G11 scFv, by the molecule to be tested, is measured by the ratio I, equal to:

$$\frac{\text{(signal in the absence of drug)} - \text{(signal in the presence of drug)}}{\text{(signal in the absence of drug)}}$$

The results are as follows:

2990 molecules do not produce any inhibition (I=1±0.2)

8 molecules produce a weak inhibition (0.4<I<0.8)

2 molecules produce a strong inhibition (I≤0.3).

2) Verification of the Modulatory Capacity of the Selected Molecules, In Vivo, in Cell Culture The in vivo verification of the modulatory capacity of the molecules selected via ELISA was carried out by means of a mast cell degranulation test, by measuring the release of β-hexosaminidase as described in Dauvillier et al., mentioned above.

In addition, the effect of the molecules selected by ELISA on total protein tyrosine phosphorylation and tyrosine phosphorylation of the Syk, PLCγ-2 and MAPK proteins was analyzed as described in Dauvillier et al., mentioned above.

Briefly, RBL-2H3 cells (rat basophil leukemia line) are seeded into a 96-well plate at a rate of $2 \times 10^5$ cells/well. They are sensitized in the presence of an anti-DNP monoclonal IgE antibody, overnight at 37° C. The cells are then incubated for 2 hours at 37° C., in the presence of various concentrations of the molecule selected by ELISA, and they are then activated with the DNP-BSA antigen, for 3 minutes at 37° C. The culture supernatant is then harvested and stored at 4° C. (S1). The adherent cells are lysed in the presence of a lysis buffer containing 0.1% of Triton X-100 and protease inhibitors. The cell lysates are also harvested and stored at 4° C. (S2).

To calculate the amount of the β-hexosaminidase enzyme released, the solutions S1 and S2 are incubated with the enzyme substrate: 4-nitrophenyl-2-deoxy-β-D-gluco-pyranoside, for 1 h 30 at 37° C. The enzyme reaction is stopped by adding a solution of glycine, pH 3, and the optical density is read at 405 nm. The amount of β-hexosaminidase released corresponds to:

$$\frac{\text{Hex } S1}{(\text{Hex } S1 + \text{Hex } S2)} \times 100$$

For each concentration, a degranulation test with a calcium ionophore (ionomycin) was carried out as control.

Figure 4:
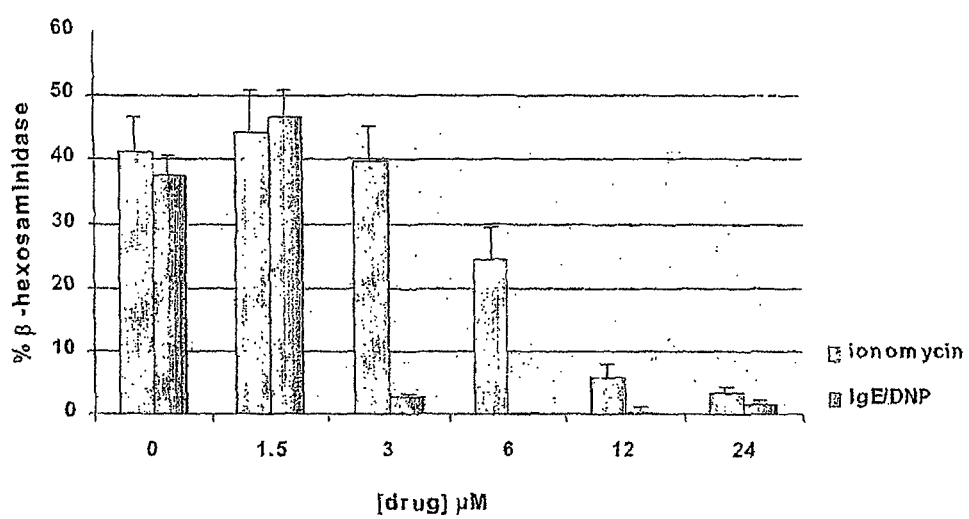
FIG. 4 illustrates the validation of the method according to the invention using the Syk protein as a target and the G4G11 scFv fragment as an antibody for screening a combinatorial library. Among the 10 molecules derived from the screening by ELISA, at least one of them strongly inhibits the release of inflammation mediators in the beta-hexosaminidase release test: at the concentration of 3 µM, the drug gives 93% inhibition of the degranulation induced by IgE, but not that induced by ionomycin.

Among the ten molecules, derived from the ELISA screening, having a ratio I≤0.8, one of them strongly inhibits β-hexosaminidase release, as shown in FIG. 4. Specifically, this molecule inhibits 93% of the IgE-induced degranulation, at a concentration of 3 μM, but does not affect the ionomycin-induced degranulation.

Figure 5:
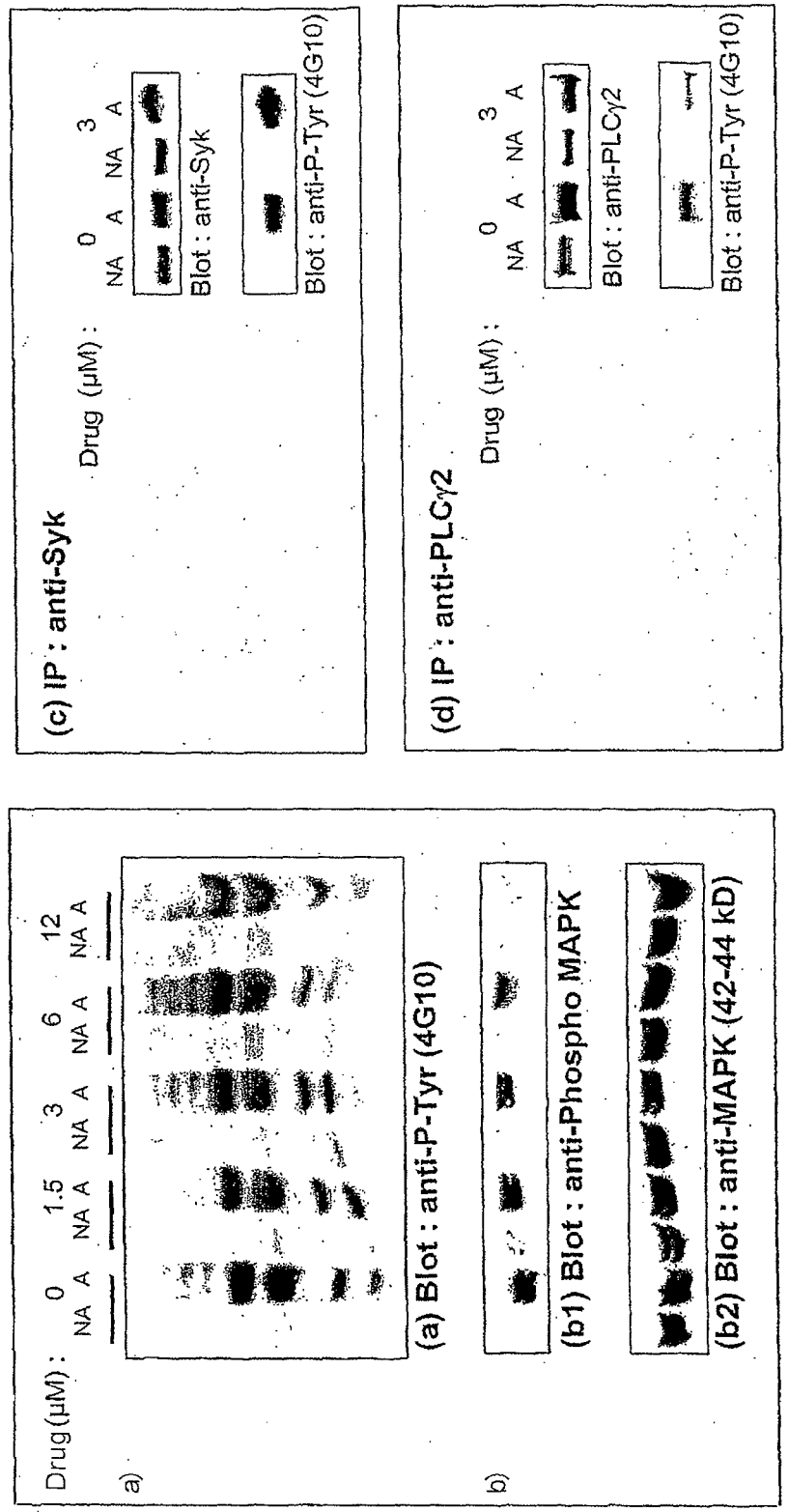
FIG. 5 illustrates the comparison of the biological effects of the drug with the inhibition observed with the scFv. Lysates of RBL-2H3 cells that are nonactivated (NA) and activated (A), in the presence of the molecule selected by ELISA (drug) at a final concentration of 1.5 to 12 µM (a and b) or 3 µM (c and d), or in the absence of this molecule, were analyzed by: a and b: immunoblotting using an anti-phosphotyrosine antibody 4G10 (a), an anti-phosphoMAPK antibody (b1) or an anti-MAPK antibody (b2); c and d: immunoprecipitation using an anti-Syk antibody (c) or an anti-PLC-γ2 antibody (d), and then immunoblotting using the same antibody used as a control, or the anti-phosphotyrosine antibody 4G10.

Supplementary assays showed that the molecule identified behaves, in vivo, like the G4G11 scFv and inhibits the PLC-γ-dependent pathway, without affecting the Ras-dependent pathway (FIG. 5). Specifically:

it does not affect the overall protein phosphorylation (FIG. 5a), it does not affect the phosphorylation of Syk (FIG. 5c), it does not affect the phosphorylation of MAPK (FIG. 5b), it decreases the phosphorylation of PLC-γ (FIG. 5d).

3) Verification of the Modulatory Capacity of the Selected Molecules, In Vivo, in Mice.

The ability of the most active molecule of FIG. 4, to inhibit systemic anaphylactic shock, was tested in BALB/c mice.

More specifically, a group of mice (group 1) was given an injection of anti-DNP monoclonal IgE, intravenously, at a rate of 100 μg per BALB/c mouse. Forty-seven hours later, and one hour before injection of the DNP antigen, the molecule was administered orally, at a rate of 100 mg/kg, in a single dose. One hour after administration of the molecule, the DNP antigen containing 2% Evans blue was injected intravenously, at a rate of 1 mg per mouse. Three groups of control mice were tested in parallel with group 1, namely:

group 2: BALB/c mice given no drug, for measuring the maximum anaphylactic shock (positive control).

group 3: BALB/c mice given an inactive molecule.

group 4: mice given IgE but not the DNP antigen (negative control).

The effect of the molecule on anaphylactic shock was then determined by measuring the release of the Evans blue, by extravasation. To do this, the mice were sacrificed and their ears were cut off. Equal surface areas of the ears were removed using a hole punch, and they were then chopped up and placed in a solution of formamide, overnight at 55° C. The following day, the release of Evans blue into the formamide solution was determined by measuring the optical density at 610 nm.

The results show a 70% decrease in extravasation of the Evans blue in the mice that were given the active molecule in the mast cell degranulation inhibition test (FIG. 4), compared with the control mice given no molecule or an inactive molecule. These results demonstrate the ability of the molecule selected by means of the screening method according to the invention, to protect an animal against anaphylactic shock.

The invention claimed is:

1. A method for identifying a non-peptide small organic molecule having a molecular mass of less than 2500 Da which selectively modulates a functional cascade in a cell involving a target protein, comprising at least the following steps:

a) identifying an intracellular antibody or an intracellular antibody fragment comprising at least one of the variable domains of an immunoglobulin chain, which binds to said target protein and modulates said functional cascade involving said target protein by inhibiting a protein-protein interaction, b) high-throughput screening, utilizing a library of small organic molecules, non-peptide small organic molecules having a molecular mass of less than 2500 Da that modulate the binding between said target protein and the antibody or the antibody fragment identified in a), and c) identifying, from the modulatory small organic molecules obtained in b), those which selectively modulate said functional cascade.

2. The method as claimed in claim 1, wherein said target protein or else the intracellular antibody or the intracellular antibody fragment are immobilized on an appropriate support and/or labeled by any means for obtaining a measurable signal.

3. The method as claimed in claim 1, wherein the identification of said intracellular antibody or intracellular antibody fragment in a) is carried out by screening a library of scFv.

4. The method as claimed in claim 3, wherein said screening is carried out using cells modified with a vector for expression of said library of scFv.

5. The method as claimed in claim 1, wherein the screening step b) comprises:
bringing the library of small organic molecules to be tested into contact with the target protein,
adding the intracellular antibody or the intracellular antibody fragment, and
measuring the relative amount of the intracellular antibody or the intracellular antibody fragment bound to the target protein, in the presence or absence of said library of small organic molecules.

6. The method as claimed in claim 1, wherein the screening step b) comprises:
bringing the intracellular antibody or intracellular antibody fragment into contact with the target protein,
adding the library of small organic molecules to be tested so as to detect the molecules capable of displacing the intracellular antibody or the intracellular antibody fragment from its complex with the target protein, and
measuring, by any appropriate means, the relative amount of antibody bound to the target protein, in the presence or absence of said library of small organic molecules.

7. The method as claimed claim 1, wherein the screening step b) comprises:
mixing the intracellular antibody or intracellular antibody fragment with the library of small organic molecules to be tested,
bringing the mixture into contact with the target protein, and
measuring, by any appropriate means, the relative amount of intracellular antibody or intracellular antibody fragment bound to the target protein, in the presence or absence of said library of small organic molecules.

8. The method as claimed in claim 1, wherein steps a) and c) are carried out by a functional test for measuring the biological activity resulting from said functional cascade by a test in a cell system.

9. The method as claimed claim 1, wherein said target protein is selected from the group consisting of: an enzyme, a receptor, an adaptor protein, and a transporter protein.

10. The method as claimed in claim 1, wherein said intracellular antibody or intracellular antibody fragment identified in a) is directed against the SH2 domains of the Syk protein and specifically inhibits the PLCγ-2 pathway.

11. The method as claimed in claim 1, wherein the identification of said intracellular antibody or intracellular antibody fragment in a) is carried out by screening a scFv phage display library.

* * * * *